United States Patent [19]

Kletecka

[11] 4,060,552

[45] Nov. 29, 1977

[54] PREPARATION OF N,N'-di-2-NAPHTHYL-p-PHENYLENEDIAMINE

[75] Inventor: George Kletecka, Rocky River, Ohio

[73] Assignee: The B. F. Goodrich Company, Akron, Ohio

[21] Appl. No.: 640,053

[22] Filed: Dec. 12, 1975

[51] Int. Cl.$^2$ .................................................. C07C 87/64
[52] U.S. Cl. .................................................. 260/576
[58] Field of Search .......................................... 260/576

[56] References Cited

U.S. PATENT DOCUMENTS 1,885,355  11/1932  Jones ..................................... 260/576

FOREIGN PATENT DOCUMENTS 1,190,274  4/1970  United Kingdom ................. 260/576

Primary Examiner—Allen B. Curtis
Assistant Examiner—John J. Doll
Attorney, Agent, or Firm—J. Hughes Powell, Jr.

[57] ABSTRACT

An improved method for the reaction of β-naphthol with p-phenylenediamine to produce N,N'-di-2-naphthyl-p-phenylenediamine at lower temperatures and with decreased formation of undesirable by-products is accomplished by reacting with said materials in the presence of boric anhydride or boric acid.

7 Claims, No Drawings

PREPARATION OF N,N'-DI-2-NAPHTHYL-P-PHENYLENEDIAMINE

BACKGROUND OF THE INVENTION

The condensation reaction of β-naphthol and p-phenylenediamine to form N,N'-di-2-naphthyl-p-phenylenediamine under the influence of heat is well known. To obtain reasonable yields of the desired product the reaction is normally conducted at high temperatures. As a consequence of reaction at such temperatures there is formed substantial amounts of undesirable by-product as β-naphthylamine.

SUMMARY OF THE INVENTION

It has now been found that when β-naphthol and p-phenylenediamine are reacted in the presence of boric anhydride or boric acid that high yields of the desired N,N'-di-2-naphthyl-p-phenylenediamine may be obtained at lower temperatures and with the formation of less undesirable β-naphthylamine.

DETAILED DESCRIPTION

The reaction of β-naphthol and p-phenylenediamine may be conducted in heated reactors, either in the melt phase or with inert solvents or diluents. Suitable diluents include aromatic solvents such as benzene, toluene, xylene and the like. The molar ratio of β-naphthol to p-phenylenediamine preferably is greater than 1:1 and more preferably 2:1, as in the range of about 3:1 to 6:1.

The essential component to provide the advantages of this invention are a boron oxide either as the boric oxide anhydride or acid. The amounts used may be as low as about 0.1 weight part per 100 weight parts of β-naphthol to about 5 or more weight parts per 100 weight parts of reactants. While larger amounts may be used, they are not necessary and excessive amounts greater than about 10% may produce reaction products that are difficult to handle. It has been found that the better the agitation in the reaction, the less boric oxide that is required.

The reaction may be conducted under varied reactor pressures but is readily conducted at about atmospheric pressure. While the reaction may be conducted at any temperature greater than about 200° C., an advantage of the use of boric oxide is that lower temperatures may be used so that normally the temperature employed is from about 200° C. to less than about 300° C., as about 250° C., although higher temperatures may be used if desired.

After the reaction is complete, the molten or solution reaction product may be mixed directly with a solvent, for example, methanol, but more preferably the molten product is cooled, broken up, and ground to a powder for example, and then contacted with an alcohol such as methanol or other suitable solvents to remove unreacted reactants, the boric oxide and undesirable by-products. Mixtures of alkanols and alkylated benzene readily remove colored impurities, for example, ethylene glycol or methanol with xylene. This extraction process may be in any standard equipment and be a batch or continuous operation. After treating with the solvent, the reaction product is isolated by filtration and may be dried for example in a vacuum oven at 60° C. and 10 mm mercury pressure.

When methanol is used as the solvent it removes any unreacted β-naphthol and forms trimethyl borate from the boric oxide which is soluble in the alcohol and is then removed with the alcohol.

To demonstrate a typical embodiment of the practice of the invention a heated reaction vessel, equipped with an agitator, thermal well, distillation head and receiver for water removal, was charged with 183.5 grams of β-naphthol (1.27 mols) and heated until melted at 120° C. There was then added to the molten β-naphthol 34.37 grams of p-phenylenediamine (0.318 mol) and 5.5 grams of boric oxide, anhydride, (0.5% by weight on the β-naphthol) and heating continued with agitation until 200° C. The reaction was held at this temperature for 4 hours. At the end of the reaction period the molten batch was poured onto a metal surface where it solidified. The solid was ground to a fine powder. 150 grams of this powder was stirred as a slurry with 320 grams of a 75% xylene and 25% methanol mixture and refluxed for 15 minutes. The slurry was then cooled to room temperature and filtered. The wet filter cake was washed with methanol, reslurried with methanol and filtered again. The wet filter cake was dried in a vacuum oven at 60° C. and 10 mm mercury pressure. A 92.9% yield of N,N'-di-2-naphthyl-p-phenylenediamine based on the p-phenylenediamine charged was obtained. The β-naphthylamine content of this reaction mixture was only about 15 ppm and after washing with methanol was less than 0.5 ppm.

In a prior art process, 3 mols of β-naphthol and 1 mol of p-phenylenediamine were heated together at 343° C. for 1.5 hours. 1259 ppm of undesirable β-naphthylamine was formed. It is difficult to remove this much material from the desired reaction product. When the reaction was conducted at 304° C. for 4 hours, 715 ppm of β-naphthylamine were formed. The yield for this 4 hour reaction was 94.3%. When this reaction was conducted for 4 hours at 232° C. the yield was only 68.9%.

This reaction at 232° C. was repeated with naphthylamine sulfonic acid, which increased the yield of desired product to 91%, but the β-naphthylamine content of the reaction product was 1237 ppm.

To demonstrate the advantages of the boric oxide of this invention a series of runs following the procedure above were made as follows. A mol ratio of β-naphthol to p-phenylenediamine of 3:1 was used in these examples.

| $B_2O_3$ conc. Wt. % of β-naphthol | Reaction Temp. ° C. | Reaction Time Hours | % Yield NPD* | β-naphthylamine parts/million |
| --- | --- | --- | --- | --- |
| 0.5 | 232 | 2 | 84 | 106 |
| 5.0 | 232 | 2 | 93 | 8 |
| 5.0 | 200 | 4 | 92 | 14.7 |

*N,N'-di-2-naphthyl-p-phenylenediamine

In another run using a molar ratio of 4:1 of β-naphthol to p-phenylenediamine with 3% $B_2O_3$, based on the weight of β-naphthol, at 200° C., and a reaction time of 4 hours, a 94% yield was obtained with only 6 ppm β-naphthylamine being formed.

To compare the results obtained with the boric oxide anhydride and boric acid, two reactions were conducted. The recipe for the boric oxide anhydride was: 275 grams of β-naphthol, 68.75 grams of p-phenylenediamine and 1.375 grams of $B_2O_3$ reacted at 232° C. for 4 hours. The yield of N,N'-di-2-naphthyl-p-phenylenediamine was 92.5%. This reaction was repeated with 1.375 grams of boric acid. The yield of N,N'-di-2-naphthyl-p-phenylenediamine in this reaction was 84.7%.

N,N'-di-2-naphthyl-p-phenylenediamine is a well known antioxidant for petroleum products, synthetic and natural rubber articles, nylon, polyolefins and the like. It is particularly useful in light colored articles.

I claim:

1. In a process for reacting β-naphthol with p-phenylenediamine to form N,N'-di-2-naphthyl-p-phenylenediamine the improvement which comprises including a boric oxide in the reaction.

2. A process of claim 1 wherein the boric oxide is boric anhydride or boric acid in amount from about 0.1 to less than 10 weight parts per 100 weight parts of β-naphthol.

3. A process of claim 2 wherein the molar ratio of β-naphthol to p-phenylenediamine is from 2:1 to about 6:1 and the reaction temperature is less than about 300° C.

4. A process of claim 3 wherein the molar ratio of β-naphthol to p-phenylenediamine is from 3:1 to 5:1, the boric oxide is boric anhydride in amounts of 0.5 to 5 weight parts per 100 weight parts of β-naphthol and the temperature is in the range of 200° C. to 250° C.

5. The process of claim 4 wherein the N,N'-di-2-naphthyl-p-phenylenediamine contains less than 100 ppm of β-naphthylamine and is treated with an alcohol containing less than 5 carbon atoms and dried.

6. A process of claim 4 wherein there is about a 4:1 molar ratio of β-naphthol to p-phenylenediamine with boric anhydride in amount of about 5% or less at a temperature of about 200° C.

7. A process of claim 6 wherein the reaction product of said β-naphthol and p-phenylenediamine is treated with an alcohol after the reaction to remove impurities including β-naphthylamine to less than 5 ppm.

* * * * *